United States Patent
Jiang et al.

(10) Patent No.: US 10,151,000 B2
(45) Date of Patent: Dec. 11, 2018

(54) ARTIFICIAL SYNTHETIC CDNA AND METHOD FOR DETECTING SECONDARY GLIOBLASTOMA

(71) Applicants: BEIJING NEUROSURGICAL INSTITUTE, Beijing (CN); BEIJING INSTITUTE FOR BRAIN DISORDERS, Beijing (CN)

(72) Inventors: Tao Jiang, Beijing (CN); Zhaoshi Bao, Beijing (CN)

(73) Assignees: Beijing Neurosurgical Institute, Beijing (CN); Beijing Institute for Brain Disorders, Beijing (CN)

( * ) Notice: Subject to any disclaimer, the term of this patent is extended or adjusted under 35 U.S.C. 154(b) by 535 days.

(21) Appl. No.: 14/800,563

(22) Filed: Jul. 15, 2015

(65) Prior Publication Data
US 2016/0017436 A1    Jan. 21, 2016

(30) Foreign Application Priority Data
Jul. 18, 2014    (CN) .......................... 2014 1 0342399

(51) Int. Cl.
| | |
|---|---|
| *C12P 19/34* | (2006.01) |
| *C12Q 1/6886* | (2018.01) |
| *C12N 9/16* | (2006.01) |
| *C12N 9/12* | (2006.01) |
| *G01N 33/574* | (2006.01) |

(52) U.S. Cl.
CPC ............ *C12Q 1/6886* (2013.01); *C12N 9/12* (2013.01); *C12N 9/16* (2013.01); *G01N 33/57407* (2013.01); *C12Q 2600/158* (2013.01); *C12Y 207/10001* (2013.01); *C12Y 301/03048* (2013.01); *G01N 2333/912* (2013.01); *G01N 2333/916* (2013.01)

(58) Field of Classification Search
None
See application file for complete search history.

(56) References Cited

U.S. PATENT DOCUMENTS

2017/0044621 A1*    2/2017    Cerami ................ C12Q 1/6886

OTHER PUBLICATIONS

Louis, D. et al., "The 2007 WHO Classification of Tumours of the Central Nervous System," Acta Neuropathologica, vol. 114, No. 2, Aug. 2007, Available Online Jul. 2007, 13 pages.
Yan, H. et al., "IDH1 and IDH2 Mutations in Gliomas," New England Journal of Medicine, vol. 360, No. 8, Feb. 2009, 15 pages.
McPherson, A. et al., "deFuse: An Algorithm for Gene Fusion Discovery in Tumor RNA-Seq Data," PLOS Computational Biology, vol. 7, No. 5, May 2011, 16 pages.
Singh, D. et al., "Transforming Fusions of FGFR and TACC Genes in Human Glioblastoma," Science, vol. 337, No. 6099, Sep. 2012, Available Online Jul. 2012, 10 pages.
Parker, B. et al., "The Tumorigenic FGFR3-TACC3 Gene Fusion Escapes miR-99a Regulation in Glioblastoma," Journal of Clinical Investigation, vol. 123, No. 2, Feb. 2013, Available Online Jan. 2013, 11 pages.
Bao, Z. et al., "RNA-seq of 272 Gliomas Revealed a Novel, Recurrent PTPRZ1-MET Fusion Transcript in Secondary Glioblastomas," Genome Research, vol. 24, No. 11, Nov. 2014, Available Online Aug. 2014, 10 pages.

* cited by examiner

*Primary Examiner* — Kenneth R Horlick
(74) *Attorney, Agent, or Firm* — McCoy Russell LLP

(57) ABSTRACT

The present invention provides an artificial synthetic cDNA (complementary deoxyribonucleic acid). The said artificial synthetic cDNA encodes a fused protein which is specifically presented in secondary glioblastoma, and the said artificial synthetic cDNA can be used as a biomarker for detecting the secondary glioblastoma. The present invention further provides a method for detecting secondary glioblastoma. According to the above technical solutions, the accuracy in distinguishing the secondary glioblastoma from primary glioblastoma is effectively improved in the present invention.

1 Claim, 1 Drawing Sheet

Specification includes a Sequence Listing.

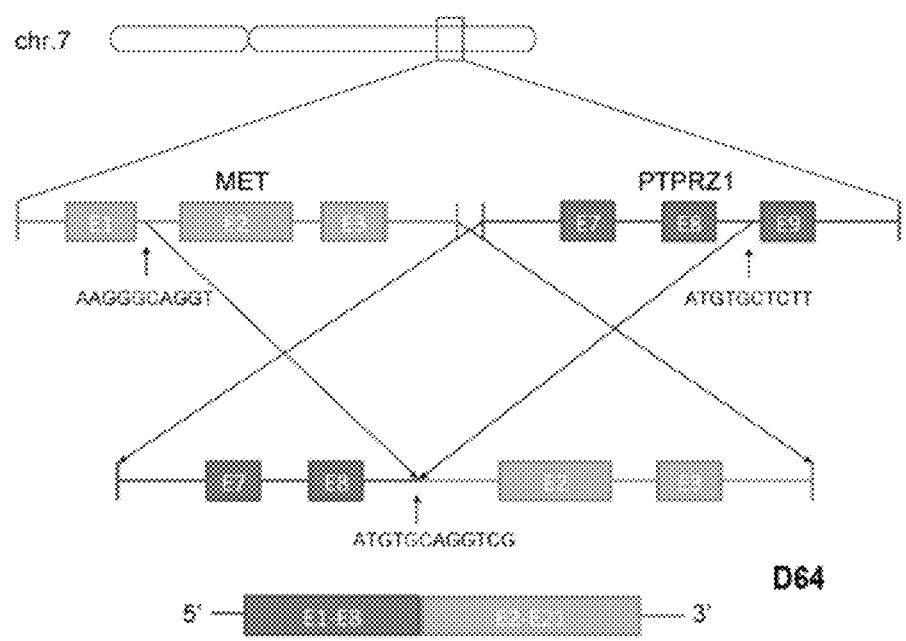

SEQUENCE LISTING

```
<160> NUMBER OF SEQ ID NOS: 18

<210> SEQ ID NO 1
<211> LENGTH: 24
<212> TYPE: PRT
<213> ORGANISM: Artificial
<220> FEATURE:
<223> OTHER INFORMATION: This sequence is synthesized in lab.

<400> SEQUENCE: 1

Met Arg Ile Leu Lys Arg Phe Leu Ala Cys Ile Gln Leu Leu Cys Val
1               5                   10                  15

Cys Arg Leu Asp Lys Pro Leu Ile
            20

<210> SEQ ID NO 2
<211> LENGTH: 46
<212> TYPE: PRT
<213> ORGANISM: Artificial
<220> FEATURE:
<223> OTHER INFORMATION: This sequence is synthesized in lab.
```

<400> SEQUENCE: 2

```
Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Asp Lys Pro Leu Ile
        35                  40                  45
```

<210> SEQ ID NO 3
<211> LENGTH: 106
<212> TYPE: PRT
<213> ORGANISM: Artificial
<220> FEATURE:
<223> OTHER INFORMATION: This sequence is synthesized in lab.

<400> SEQUENCE: 3

```
Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Asp Lys Pro Leu Ile
            100                 105
```

<210> SEQ ID NO 4
<211> LENGTH: 314
<212> TYPE: PRT
<213> ORGANISM: Artificial
<220> FEATURE:
<223> OTHER INFORMATION: This sequence is synthesized in lab.

<400> SEQUENCE: 4

```
Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
        115                 120                 125

His Trp Gly Lys Cys Asn Met Ser Ser Asp Gly Ser Glu His Ser Leu
    130                 135                 140
```

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Val Gly Thr Glu Glu Asn Leu Asp
        180                 185                 190

Phe Lys Ala Ile Ile Asp Gly Val Glu Ser Val Ser Arg Phe Gly Lys
            195                 200                 205

Gln Ala Ala Leu Asp Pro Phe Ile Leu Leu Asn Leu Leu Pro Asn Ser
        210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
                245                 250                 255

Glu Ser Gln Leu Ala Val Phe Cys Glu Val Leu Thr Met Gln Gln Ser
                260                 265                 270

Gly Tyr Val Met Leu Met Asp Tyr Leu Gln Asn Asn Phe Arg Glu Gln
            275                 280                 285

Gln Tyr Lys Phe Ser Arg Gln Val Phe Ser Ser Tyr Thr Gly Lys Glu
        290                 295                 300

Glu Ile His Glu Ala Asp Lys Pro Leu Ile
305                 310

<210> SEQ ID NO 5
<211> LENGTH: 1390
<212> TYPE: PRT
<213> ORGANISM: Artificial
<220> FEATURE:
<223> OTHER INFORMATION: This sequence is synthesized in lab.

<400> SEQUENCE: 5

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65              70                  75                  80

Val Ala Glu Tyr Lys Thr Gly Pro Val Leu Glu His Pro Asp Cys Phe
            85                  90                  95

Pro Cys Gln Asp Cys Ser Ser Lys Ala Asn Leu Ser Gly Gly Val Trp
        100                 105                 110

Lys Asp Asn Ile Asn Met Ala Leu Val Val Asp Thr Tyr Tyr Asp Asp
    115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

```
Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605
```

```
Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp Gln Phe Pro Asn Ser  Ser Gln Asn Gly Ser  Cys Arg Gln
    1010                1015                1020

Val Gln Tyr Pro Leu Thr Asp Met Ser Pro Ile Leu  Thr Ser Gly
```

```
                1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 6
<211> LENGTH: 1408
<212> TYPE: PRT
<213> ORGANISM: Artificial
```

<220> FEATURE:
<223> OTHER INFORMATION: This sequence is synthesized in lab.

<400> SEQUENCE: 6

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

```
Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
            565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
            805                 810                 815
```

```
Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
        850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
        915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
            965                 970                 975

Lys Gln Ile Lys Asp Leu Gly Ser Glu Leu Val Arg Tyr Asp Ala Arg
        980                 985                 990

Val His Thr Pro His Leu Asp Arg Leu Val Ser Ala Arg Ser Val Ser
            995                 1000                1005

Pro Thr Thr Glu Met Val Ser Asn Glu Ser Val Asp Tyr Arg Ala
    1010                1015                1020

Thr Phe Pro Glu Asp Gln Phe Pro Asn Ser Ser Gln Asn Gly Ser
    1025                1030                1035

Cys Arg Gln Val Gln Tyr Pro Leu Thr Asp Met Ser Pro Ile Leu
    1040                1045                1050

Thr Ser Gly Asp Ser Asp Ile Ser Ser Pro Leu Leu Gln Asn Thr
    1055                1060                1065

Val His Ile Asp Leu Ser Ala Leu Asn Pro Glu Leu Val Gln Ala
    1070                1075                1080

Val Gln His Val Val Ile Gly Pro Ser Ser Leu Ile Val His Phe
    1085                1090                1095

Asn Glu Val Ile Gly Arg Gly His Phe Gly Cys Val Tyr His Gly
    1100                1105                1110

Thr Leu Leu Asp Asn Asp Gly Lys Lys Ile His Cys Ala Val Lys
    1115                1120                1125

Ser Leu Asn Arg Ile Thr Asp Ile Gly Glu Val Ser Gln Phe Leu
    1130                1135                1140

Thr Glu Gly Ile Ile Met Lys Asp Phe Ser His Pro Asn Val Leu
    1145                1150                1155

Ser Leu Leu Gly Ile Cys Leu Arg Ser Glu Gly Ser Pro Leu Val
    1160                1165                1170

Val Leu Pro Tyr Met Lys His Gly Asp Leu Arg Asn Phe Ile Arg
    1175                1180                1185

Asn Glu Thr His Asn Pro Thr Val Lys Asp Leu Ile Gly Phe Gly
    1190                1195                1200

Leu Gln Val Ala Lys Gly Met Lys Tyr Leu Ala Ser Lys Lys Phe
    1205                1210                1215

Val His Arg Asp Leu Ala Ala Arg Asn Cys Met Leu Asp Glu Lys
```

Phe Thr Val Lys Val Ala Asp Phe Gly Leu Ala Arg Asp Met Tyr
1235                1240                1245

Asp Lys Glu Tyr Tyr Ser Val His Asn Lys Thr Gly Ala Lys Leu
1250                1255                1260

Pro Val Lys Trp Met Ala Leu Glu Ser Leu Gln Thr Gln Lys Phe
1265                1270                1275

Thr Thr Lys Ser Asp Val Trp Ser Phe Gly Val Leu Leu Trp Glu
1280                1285                1290

Leu Met Thr Arg Gly Ala Pro Pro Tyr Pro Asp Val Asn Thr Phe
1295                1300                1305

Asp Ile Thr Val Tyr Leu Leu Gln Gly Arg Arg Leu Leu Gln Pro
1310                1315                1320

Glu Tyr Cys Pro Asp Pro Leu Tyr Glu Val Met Leu Lys Cys Trp
1325                1330                1335

His Pro Lys Ala Glu Met Arg Pro Ser Phe Ser Glu Leu Val Ser
1340                1345                1350

Arg Ile Ser Ala Ile Phe Ser Thr Phe Ile Gly Glu His Tyr Val
1355                1360                1365

His Val Asn Ala Thr Tyr Val Asn Val Lys Cys Val Ala Pro Tyr
1370                1375                1380

Pro Ser Leu Leu Ser Ser Glu Asp Asn Ala Asp Asp Glu Val Asp
1385                1390                1395

Thr Arg Pro Ala Ser Phe Trp Glu Thr Ser
1400                1405

<210> SEQ ID NO 7
<211> LENGTH: 72
<212> TYPE: DNA
<213> ORGANISM: Artificial
<220> FEATURE:
<223> OTHER INFORMATION: This sequence is synthesized in lab.

<400> SEQUENCE: 7
atgcgaatcc taaagcgttt cctcgcttgc attcagctcc tctgtgtttg ccgcctggat    60
aaacctctca ta                                                        72

<210> SEQ ID NO 8
<211> LENGTH: 138
<212> TYPE: DNA
<213> ORGANISM: Artificial
<220> FEATURE:
<223> OTHER INFORMATION: This sequence is synthesized in lab.

<400> SEQUENCE: 8
atgcgaatcc taaagcgttt cctcgcttgc attcagctcc tctgtgtttg ccgcctggat    60
tgggctaatg gatactacag acaacagaga aaacttgttg aagagattgg ctggtcctat   120
acagataaac ctctcata                                                 138

<210> SEQ ID NO 9
<211> LENGTH: 318
<212> TYPE: DNA
<213> ORGANISM: Artificial
<220> FEATURE:
<223> OTHER INFORMATION: This sequence is synthesized in lab.

<400> SEQUENCE: 9
atgcgaatcc taaagcgttt cctcgcttgc attcagctcc tctgtgtttg ccgcctggat    60

```
tgggctaatg gatactacag acaacagaga aaacttgttg aagagattgg ctggtcctat      120
acaggagcac tgaatcaaaa aaattgggga agaaatatc  caacatgtaa tagcccaaaa      180
caatctccta tcaatattga tgaagatctt acacaagtaa atgtgaatct taagaaactt      240
aaatttcagg gttgggataa aacatcattg gaaaacacat tcattcataa cactgggaaa      300
acagataaac ctctcata                                                    318
```

<210> SEQ ID NO 10
<211> LENGTH: 942
<212> TYPE: DNA
<213> ORGANISM: Artificial
<220> FEATURE:
<223> OTHER INFORMATION: This sequence is synthesized in lab.

<400> SEQUENCE: 10

```
atgcgaatcc taaagcgttt cctcgcttgc attcagctcc tctgtgtttg ccgcctggat       60
tgggctaatg gatactacag acaacagaga aaacttgttg aagagattgg ctggtcctat      120
acaggagcac tgaatcaaaa aaattgggga agaaatatc  caacatgtaa tagcccaaaa      180
caatctccta tcaatattga tgaagatctt acacaagtaa atgtgaatct taagaaactt      240
aaatttcagg gttgggataa aacatcattg gaaaacacat tcattcataa cactgggaaa      300
acagtggaaa ttaatctcac taatgactac cgtgtcagcg gagagtttc  agaaatggtg      360 tttaaagcaa gcaagataac ttttcactgg ggaaaatgca atatgtcatc tgatggatca      420
gagcatagtt tagaaggaca aaaatttcca cttgagatgc aaatctactg ctttgatgcg      480
gaccgatttt caagttttga ggaagcagtc aaaggaaaag ggaagttaag agctttatcc      540
attttgtttg aggttgggac agaagaaaat ttggatttca aagcgattat tgatggagtc      600
gaaagtgtta gtcgttttgg gaagcaggct gctttagatc cattcatact gttgaacctt      660
ctgccaaact caactgacaa gtattacatt tacaatggct cattgacatc tcctccctgc      720
acagacacag ttgactggat tgttttttaaa gatacagtta gcatctctga aagccagttg      780 gctgttttttt gtgaagttct tacaatgcaa caatctggtt atgtcatgct gatggactac      840
ttacaaaaca attttcgaga gcaacagtac aagttctcta gacaggtgtt ttcctcatac      900
actggaaagg aagagattca tgaagcagat aaacctctca ta                         942
```

<210> SEQ ID NO 11
<211> LENGTH: 4173
<212> TYPE: DNA
<213> ORGANISM: Artificial
<220> FEATURE:
<223> OTHER INFORMATION: This sequence is synthesized in lab.

<400> SEQUENCE: 11

```
atgaaggccc ccgctgtgct tgcacctggc atcctcgtgc tcctgtttac cttggtgcag       60
aggagcaatg gggagtgtaa agaggcacta gcaaagtccg agatgaatgt gaatatgaag      120
tatcagcttc ccaacttcac cgcggaaaca cccatccaga atgtcattct acatgagcat      180
cacattttcc ttggtgccac taactacatt tatgttttaa atgaggaaga ccttcagaag      240
gttgctgagt acaagactgg gcctgtgctg aacacccag  attgtttccc atgtcaggac      300
tgcagcagca agccaattt  atcaggaggt gtttggaaag ataacatcaa catggctcta      360
gttgtcgaca cctactatga tgatcaactc attagctgtg gcagcgtcaa cagagggacc      420
tgccagcgac atgtcttttcc ccacaatcat actgctgaca tacagtcgga ggttcactgc      480
```

```
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctggggc ccagcttgct agacaaatag gagccagcct gaatgatgac   1020 attctttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa   1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg aaaaacatg tactttaaaa   2100 agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg gaaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg tttttcctgt ggctgaaaaa gagaaagcaa   2880
```

| | | |
|---|---|---|
| attaaagatc tgggcagtga attagttcgc tacgatgcaa gagtacacac tcctcatttg | 2940 | |
| gataggcttg taagtgcccg aagtgtaagc ccaactacag aaatggtttc aaatgaatct | 3000 | |
| gtagactacc gagctacttt tccagaagat cagtttccta attcatctca gaacggttca | 3060 | |
| tgccgacaag tgcagtatcc tctgacagac atgtccccca tcctaactag tggggactct | 3120 | |
| gatatatcca gtccattact gcaaaatact gtccacattg acctcagtgc tctaaatcca | 3180 | |
| gagctggtcc aggcagtgca gcatgtagtg attgggccca gtagcctgat tgtgcatttc | 3240 | |
| aatgaagtca taggaagagg gcattttggt tgtgtatatc atgggacttt gttggacaat | 3300 | |
| gatggcaaga aaattcactg tgctgtgaaa tccttgaaca gaatcactga cataggagaa | 3360 | |
| gtttcccaat ttctgaccga gggaatcatc atgaaagatt ttagtcatcc caatgtcctc | 3420 | |
| tcgctcctgg gaatctgcct gcgaagtgaa gggtctccgc tggtggtcct accatacatg | 3480 | |
| aaacatggag atcttcgaaa tttcattcga aatgagactc ataatccaac tgtaaaagat | 3540 | |
| cttattggct ttggtcttca agtagccaaa ggcatgaaat atcttgcaag caaaaagttt | 3600 | |
| gtccacagag acttggctgc aagaaactgt atgctggatg aaaaattcac agtcaaggtt | 3660 | |
| gctgattttg gtcttgccag agacatgtat gataaagaat actatagtgt acacaacaaa | 3720 | |
| acaggtgcaa agctgccagt gaagtggatg gctttggaaa gtctgcaaac tcaaaagttt | 3780 | |
| accaccaagt cagatgtgtg gtcctttggc gtgctcctct gggagctgat gacaagagga | 3840 | |
| gccccacctt atcctgacgt aaacacctt gatataactg tttacttgtt gcaagggaga | 3900 | |
| agactcctac aacccgaata ctgcccagac cccttatatg aagtaatgct aaaatgctgg | 3960 | |
| caccctaaag ccgaaatgcg cccatccttt tctgaactgg tgtcccggat atcagcgatc | 4020 | |
| ttctctactt tcattgggga gcactatgtc catgtgaacg ctacttatgt gaacgtaaaa | 4080 | |
| tgtgtcgctc cgtatccttc tctgttgtca tcagaagata acgctgatga tgaggtggac | 4140 | |
| acacgaccag cctccttctg ggagacatca tag | 4173 | |

<210> SEQ ID NO 12
<211> LENGTH: 4227
<212> TYPE: DNA
<213> ORGANISM: Artificial
<220> FEATURE:
<223> OTHER INFORMATION: This sequence is synthesized in lab.

<400> SEQUENCE: 12

| | | |
|---|---|---|
| atgaaggccc ccgctgtgct tgcacctggc atcctcgtgc tcctgtttac cttggtgcag | 60 | |
| aggagcaatg gggagtgtaa agaggcacta gcaaagtccg agatgaatgt gaatatgaag | 120 | |
| tatcagcttc ccaacttcac cgcggaaaca cccatccaga atgtcattct acatgagcat | 180 | |
| cacattttcc ttggtgccac taactacatt tatgttttaa atgaggaaga ccttcagaag | 240 | |
| gttgctgagt acaagactgg gcctgtgctg gaacacccag attgtttccc atgtcaggac | 300 | |
| tgcagcagca agccaatttt atcaggaggt gtttggaaag ataacatcaa catggctcta | 360 | |
| gttgtcgaca cctactatga tgatcaactc attagctgtg gcagcgtcaa cagagggacc | 420 | |
| tgccagcgac atgtctttcc ccacaatcat actgctgaca tacagtcgga ggttcactgc | 480 | |
| atattctccc cacagataga agagcccagc cagtgtcctg actgtgtggt gagcgccctg | 540 | |
| ggagccaaag tcctttcatc tgtaaaggac cggttcatca acttctttgt aggcaatacc | 600 | |
| ataaattctt cttatttccc agatcatcca ttgcattcga tatcagtgag aaggctaaag | 660 | |
| gaaacgaaag atggttttat gtttttgacg gaccagtcct acattgatgt tttacctgag | 720 | |

```
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt ttaatatact tcaggctgcg     960
tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa   1800
actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg aaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtacttg gtggaaagaa   2280
cctctcaaca ttgtcagttt tctatttttgc tttgccagtg gtgggagcac aataacaggt   2340
gttgggaaaa acctgaattc agttagtgtc ccgagaatgg tcataaatgt gcatgaagca   2400
ggaaggaact ttacagtggc atgtcaacat cgctctaatt cagagataat ctgttgtacc   2460
actccttccc tgcaacagct gaatctgcaa ctcccctga aaaccaaagc ctttttcatg   2520
ttagatggga tccttttccaa atactttgat ctcattatg tacataatcc tgtgtttaag   2580
cctttgaaa agccagtgat gatctcaatg ggcaatgaaa atgtactgga aattaaggga   2640
aatgatattg accctgaagc agttaaaggt gaagtgttaa aagttggaaa taagagctgt   2700
gagaatatac acttacattc tgaagccgtt ttatgcacgg tccccaatga cctgctgaaa   2760
ttgaacagcg agctaaatat agagtggaag caagcaattt cttcaaccgt ccttggaaaa   2820
gtaatagttc aaccagatca gaatttcaca ggattgattg ctggtgttgt ctcaatatca   2880
acagcactgt tattactact tgggttttc ctgtggctga aaagagaaa gcaaattaaa   2940
gatctgggca gtgaattagt tcgctacgat gcaagagtac acactcctca tttggatagg   3000
cttgtaagtg cccgaagtgt aagcccaact acagaaatgg tttcaaatga atctgtagac   3060
taccgagcta cttttccaga agatcagttt cctaattcat ctcagaacgg ttcatgccga   3120
```

```
caagtgcagt atcctctgac agacatgtcc cccatcctaa ctagtgggga ctctgatata    3180
tccagtccat tactgcaaaa tactgtccac attgacctca gtgctctaaa tccagagctg    3240
gtccaggcag tgcagcatgt agtgattggg cccagtagcc tgattgtgca tttcaatgaa    3300
gtcataggaa gagggcattt tggttgtgta tatcatggga ctttgttgga caatgatggc    3360
aagaaaattc actgtgctgt gaaatccttg aacagaatca ctgacatagg agaagtttcc    3420
caatttctga ccgagggaat catcatgaaa gattttagtc atcccaatgt cctctcgctc    3480
ctgggaatct gcctgcgaag tgaagggtct ccgctggtgg tcctaccata catgaaacat    3540
ggagatcttc gaaatttcat tcgaaatgag actcataatc caactgtaaa agatcttatt    3600
ggctttggtc ttcaagtagc caaaggcatg aaatatcttg caagcaaaaa gtttgtccac    3660
agagacttgg ctgcaagaaa ctgtatgctg atgaaaaat tcacagtcaa ggttgctgat    3720
tttggtcttg ccagagacat gtatgataaa gaatactata gtgtacacaa caaaacaggt    3780
gcaaagctgc cagtgaagtg gatggctttg gaaagtctgc aaactcaaaa gtttaccacc    3840
aagtcagatg tgtggtcctt tggcgtgctc ctctgggagc tgatgacaag aggagcccca    3900
ccttatcctg acgtaaacac ctttgatata actgtttact tgttgcaagg gagaagactc    3960
ctacaacccg aatactgccc agacccctta tatgaagtaa tgctaaaatg ctggcaccct    4020
aaagccgaaa tgcgcccatc cttttctgaa ctggtgtccc ggatatcagc gatcttctct    4080
actttcattg gggagcacta tgtccatgtg aacgctactt atgtgaacgt aaaatgtgtc    4140
gctccgtatc cttctctgtt gtcatcagaa gataacgctg atgatgaggt ggacacacga    4200
ccagcctcct tctgggagac atcatag                                        4227
```

<210> SEQ ID NO 13
<211> LENGTH: 347
<212> TYPE: DNA
<213> ORGANISM: Artificial
<220> FEATURE:
<223> OTHER INFORMATION: This sequence is synthesized in lab.

<400> SEQUENCE: 13

```
ccgtctggaa atgcgaatcc taaagcgttt cctcgcttgc attcagctcc tctgtgtttg     60
ccgcctggat aaacctctca taatgaaggc ccccgctgtg cttgcacctg gcatcctcgt    120
gctcctgttt accttggtgc agaggagcaa tggggagtgt aaagaggcac tagcaaagtc    180
cgagatgaat gtgaatatga agtatcagct tcccaacttc accgcggaaa cacccatcca    240
gaatgtcatt ctacatgagc atcacatttt ccttggtgcc actaactaca tttatgtttt    300
aaatgaggaa gaccttcaga aggttgctga gtacaagact gggcctg                 347
```

<210> SEQ ID NO 14
<211> LENGTH: 413
<212> TYPE: DNA
<213> ORGANISM: Artificial
<220> FEATURE:
<223> OTHER INFORMATION: This sequence is synthesized in lab.

<400> SEQUENCE: 14

```
ccgtctggaa atgcgaatcc taaagcgttt cctcgcttgc attcagctcc tctgtgtttg     60
ccgcctggat tgggctaatg gatactacag acaacagaga aaacttgttg aagagattgg    120
ctggtcctat acagataaac ctctcataat gaaggccccc gctgtgcttg cacctggcat    180
cctcgtgctc ctgtttacct tggtgcagag gagcaatggg gagtgtaaag aggcactagc    240
```

| | |
|---|---|
| aaagtccgag atgaatgtga atatgaagta tcagcttccc aacttcaccg cggaaacacc | 300 |
| catccagaat gtcattctac atgagcatca cattttcctt ggtgccacta actacattta | 360 |
| tgttttaaat gaggaagacc ttcagaaggt tgctgagtac aagactgggc ctg | 413 |

<210> SEQ ID NO 15
<211> LENGTH: 593
<212> TYPE: DNA
<213> ORGANISM: Artificial
<220> FEATURE:
<223> OTHER INFORMATION: This sequence is synthesized in lab.

<400> SEQUENCE: 15

| | |
|---|---|
| ccgtctggaa atgcgaatcc taaagcgttt cctcgcttgc attcagctcc tctgtgtttg | 60 |
| ccgcctggat tgggctaatg gatactacag caacagaga aaacttgttg aagagattgg | 120 |
| ctggtcctat acaggagcac tgaatcaaaa aaattgggga agaaatatc caacatgtaa | 180 |
| tagcccaaaa caatctccta tcaatattga tgaagatctt acacaagtaa atgtgaatct | 240 |
| taagaaactt aaatttcagg gttgggataa acatcattg gaaaacacat tcattcataa | 300 |
| cactgggaaa acagataaac ctctcataat gaaggccccc gctgtgcttg cacctggcat | 360 |
| cctcgtgctc ctgtttacct tggtgcagag gagcaatggg gagtgtaaag aggcactagc | 420 |
| aaagtccgag atgaatgtga atatgaagta tcagcttccc aacttcaccg cggaaacacc | 480 |
| catccagaat gtcattctac atgagcatca cattttcctt ggtgccacta actacattta | 540 |
| tgttttaaat gaggaagacc ttcagaaggt tgctgagtac aagactgggc ctg | 593 |

<210> SEQ ID NO 16
<211> LENGTH: 1217
<212> TYPE: DNA
<213> ORGANISM: Artificial
<220> FEATURE:
<223> OTHER INFORMATION: This sequence is synthesized in lab.

<400> SEQUENCE: 16

| | |
|---|---|
| ccgtctggaa atgcgaatcc taaagcgttt cctcgcttgc attcagctcc tctgtgtttg | 60 |
| ccgcctggat tgggctaatg gatactacag caacagaga aaacttgttg aagagattgg | 120 |
| ctggtcctat acaggagcac tgaatcaaaa aaattgggga agaaatatc caacatgtaa | 180 |
| tagcccaaaa caatctccta tcaatattga tgaagatctt acacaagtaa atgtgaatct | 240 |
| taagaaactt aaatttcagg gttgggataa acatcattg gaaaacacat tcattcataa | 300 |
| cactgggaaa acagtggaaa ttaatctcac taatgactac cgtgtcagcg gaggagtttc | 360 |
| agaaatggtg tttaaagcaa gcaagataac ttttcactgg ggaaaatgca atatgtcatc | 420 |
| tgatggatca gagcatagtt tagaaggaca aaaatttcca cttgagatgc aaatctactg | 480 |
| ctttgatgcg gaccgatttt caagttttga ggaagcagtc aaaggaaaag ggaagttaag | 540 |
| agctttatcc attttgtttg aggttgggac agaagaaaat ttggatttca aagcgattat | 600 |
| tgatggagtc gaaagtgtta gtcgttttgg gaagcaggc gctttagatc cattcatact | 660 |
| gttgaacctt ctgccaaact caactgacaa gtattacatt tacaatggct cattgacatc | 720 |
| tcctcccctgc acagacacag ttgactggat tgttttaaa gatacagtta gcatctctga | 780 |
| aagccagttg gctgtttttt gtgaagttct tacaatgcaa caatctggtt atgtcatgct | 840 |
| gatggactac ttacaaaaca attttcgaga gcaacagtac aagttctcta gacaggtgtt | 900 |
| ttcctcatac actggaaagg aagagattca tgaagcagat aaacctctca taatgaaggc | 960 |
| ccccgctgtg cttgcacctg gcatcctcgt gctcctgttt accttggtgc agaggagcaa | 1020 |

```
tggggagtgt aaagaggcac tagcaaagtc cgagatgaat gtgaatatga agtatcagct    1080
tcccaacttc accgcggaaa cacccatcca gaatgtcatt ctacatgagc atcacatttt    1140
ccttggtgcc actaactaca tttatgtttt aaatgaggaa gaccttcaga aggttgctga    1200
gtacaagact gggcctg                                                   1217

<210> SEQ ID NO 17
<211> LENGTH: 24
<212> TYPE: DNA
<213> ORGANISM: Artificial
<220> FEATURE:
<223> OTHER INFORMATION: This sequence is synthesized in lab.

<400> SEQUENCE: 17
ccgtctggaa atgcgaatcc taaa                                             24

<210> SEQ ID NO 18
<211> LENGTH: 24
<212> TYPE: DNA
<213> ORGANISM: Artificial
<220> FEATURE:
<223> OTHER INFORMATION: This sequence is synthesized in lab.

<400> SEQUENCE: 18
caggcccagt cttgtactca gcaa                                             24
```

ARTIFICIAL SYNTHETIC CDNA AND METHOD FOR DETECTING SECONDARY GLIOBLASTOMA

CROSS-REFERENCE TO RELATED APPLICATIONS

The present application claims priority to Chinese Patent Application No. 201410342399.1, filed on Jul. 18, 2014, the entire contents of which are hereby incorporated by reference for all purposes.

INCORPORATION BY REFERENCE TO ELECTRONICALLY SUBMITTED MATERIAL

Incorporated by reference in its entirety herein is a computer-readable nucleotide/amino acid sequence listing submitted herewith and identified as follows: 47,116 bytes ASCII (Text) file named "Sequence_Listing_INN14301," created Jun. 15, 2015.

FIELD OF THE INVENTION

The present invention relates to the technical field of biotechnology and specifically relates to an artificial synthetic cDNA, a fragment of the artificial synthetic cDNA and a method for detecting secondary glioblastoma.

BACKGROUND OF THE INVENTION

Glioblastoma is glioma with the highest malignant degree in astrocytomas. This tumor locates below the cortex and grows throughout supratentorial cerebral hemisphere in most cases. This tumor grows in an infiltrative manner, often invades several cerebral lobes, and further invades the deep structure and can also affect the contralateral cerebral hemisphere via the callus. This tumor mostly grows in the frontal lobe, followed by the temporal lobe and the parietal lobe, and the tumor can also occur in the occipital lobe/the thalamus, the basal ganglia and the like in a few cases.

The glioblastoma has a high growth rate and short disease course, and for 70-80% of patients, the disease course is 3-6 months, and only 10% of the patients have a disease course of more than 1 year. In the individual cases, the stroke-like episodes may occur due to tumor bleeding. Due to rapid growth of the tumor, the hydrocephalus occurs frequently, and the symptom of increased intracranial pressure is obvious, and almost all the patients suffer from headache, vomiting, papilledema/headache, mental changes, limb weakness, unconsciousness, and speech disorders. The glioblastoma damages brain tissues in an infiltrative manner and causes a series of focal lesion symptoms, and the patients have aphasia, hemiplegia, hemianesthesia, hemianopsia and the like to different extents. Hemiplegia, brain neural damages, hemianesthesia, and hemianopsia can be found by neurological examination. About 33% of the patients have seizures and about 20% of the patients have dementia, hypophrenia, and other mental symptoms.

The glioblastoma can be divided into secondary glioblastoma developed from low-grade astrocytomas and primary glioblastoma which does not show early stage low-grade lesions. But the secondary glioblastoma and the primary glioblastoma are very difficult to be distinguished in histology. At present, although the mutation of isocitrate dehydrogenase (IDH) is only found in the secondary glioblastoma, the mutation of IDH does not occur in part of the secondary glioblastomas.

Thus, the detection of the secondary glioblastoma cannot solely rely on the detection of the mutation of IDH, and a new method for detecting secondary glioblastoma needs to be developed to improve the detection of the secondary glioblastoma.

SUMMARY OF THE INVENTION

In order to further improve the detection accuracy of secondary glioblastoma, the present invention provides an artificial synthetic cDNA, a fragment of the artificial synthetic cDNA, and a method for detecting the secondary glioblastoma.

A fused protein provided by the present invention has relatively high specificity in the appearance of the secondary glioblastoma. In one aspect, the present invention provides an artificial synthetic cDNA, and the artificial synthetic cDNA does not exist in the nature, wherein the artificial synthetic cDNA encodes a certain fused protein; and in a direction from an N terminal to a C terminal, the fused protein is formed of a first protein fragment connected to a second protein fragment, wherein the first protein fragment is as shown in SEQ ID NO: 1, 2, 3 or 4 and the second protein fragment is as shown in SEQ ID NO: 5 or 6.

In another aspect, the present invention further provides an artificial synthetic nucleic acid fragment, and the artificial synthetic nucleic acid fragment does not exist in the nature, wherein the sequence of the artificial synthetic nucleic acid fragment contains the sequence as shown in SEQ ID NO: 14, 15 or 16, and the artificial synthetic nucleic acid fragment is the fragment of the above-mentioned artificial synthetic cDNA.

In still another aspect, the present invention further provides a primer pair, wherein the primer pair contains a first primer as shown in SEQ ID NO: 17 and a second primer as shown in SEQ ID NO: 18, and 5' ends of the first primer and the second primer are chemically modified.

The present invention can also provide a method for detecting secondary glioblastoma, and the method comprises the following steps: detecting a certain fused protein in a glioblastoma sample to be detected by using an artificially prepared antibody, wherein the fused protein in the direction from an N terminal to a C terminal is formed by connecting a first protein fragment and a second protein fragment, wherein the first protein fragment is as shown in SEQ ID NO: 1, 2, 3 or 4 and the second protein fragment is as shown in SEQ ID NO: 5 or 6; and indicating that the glioblastoma sample to be detected is the secondary glioblastoma if the fused protein is presented in the glioblastoma sample to be detected.

The method may additionally or alternatively comprise the following steps:

detecting the content of a certain fused nucleic acid in a glioblastoma sample to be detected by using a chemically modified nucleic acid probe and/or primers which are prepared artificially, wherein the fused nucleic acid is the nucleic acid coding the fused protein; and indicating that the glioblastoma sample to be detected is the secondary glioblastoma if the fused nucleic acid is presented in the glioblastoma sample to be detected.

Through the above technical solution, the artificial synthetic cDNA provided by the present invention effectively improves the accuracy in distinguishing the secondary glioblastoma from primary glioblastoma.

Other features and advantages of the present invention will be described in detail in the following detailed description of the embodiments.

BRIEF DESCRIPTION OF THE DRAWING

The accompanying drawing is used for providing a further understanding of the present invention and constitutes one part of the description. The accompanying drawing and the following detailed description of the embodiments are used for explaining the present invention rather than limiting the present invention. Wherein, FIG. 1 is a structural schematic diagram of a fused protein formed by connecting a PTPRZ1 protein fragment and an MET protein fragment, which shows the three zoomed-in views of the region of the translocation and subsequent generated cDNA. The said fused protein named D64 is formed of a first protein fragment connected to a second protein fragment, the said first protein fragment is as shown in SEQ ID NO: 4 and the said second protein fragment is as shown in SEQ ID NO: 5 or 6.

DETAILED DESCRIPTION OF THE EMBODIMENTS

In conjunction with the accompanying drawing, the specific embodiments of the present invention will be described below in detail. It should be understood that the specific embodiments described herein are only intended to illustrate and explain the present invention and are not intended to limit the present invention.

In the present invention, unless contrarily indicated, the term "nucleic acid" used herein can be deoxyribonucleic acid or ribonucleic acid; the "nucleic acid" can be single-stranded nucleic acid or double-stranded nucleic acid; the sequence of the "nucleic acid" refers to the sequence of bases; and the "nucleic acid" can have the known modification in the art as long as the modification does not change the base pairing of the "nucleic acid".

According the present invention, a fused protein is provided, wherein the fused protein in the direction from an N terminal to a C terminal is formed of a first protein fragment connected to a second protein fragment, wherein the first protein fragment is as shown in SEQ ID NO: 1, 2, 3 or 4 and the second protein fragment is as shown in SEQ ID NO: 5 or 6.

SEQ ID NO: 1 is a protein sequence encoded by the coding sequence of the first exon of the human PTPRZ1 gene (whose NCBI Gene ID is 5803).

SEQ ID NO: 2 is the protein sequence encoded by the coding sequence from the first exon to the second exon of the human PTPRZ1 gene.

SEQ ID NO: 3 is the protein sequence encoded by the coding sequence from the first exon to the third exon of the human PTPRZ1 gene.

SEQ ID NO: 4 is the protein sequence encoded by the coding sequence from the first exon to the eighth exon of the human PTPRZ1 gene.

SEQ ID NO: 5 is a fragment of the protein sequence encoded by the sequence from the start of exon 2 to the end of the translated region of the homology isoform 1 of the human MET gene (whose NCBI Gene ID is 4233).

SEQ ID NO: 6 is the fragment of the encoded protein sequence encoded by the sequence from the start of exon 2 to the end of the translated region of the homology isoform 2 of the human MET gene.

In one aspect, the present invention provides an artificial synthetic cDNA, and the artificial synthetic cDNA does not exist in the nature, wherein the artificial synthetic cDNA encodes a certain fused protein; and the fused protein in the direction from an N terminal to a C terminal is formed of a first protein fragment connected to a second protein fragment, wherein the first protein fragment is as shown in SEQ ID NO: 1, 2, 3 or 4 and the second protein fragment is as shown in SEQ ID NO: 5 or 6.

The artificial synthetic cDNA does not exist in nature, including the situation that the artificial synthetic cDNA does not exist in a genomic DNA sequence. The production of the sequence of the artificial synthetic cDNA may include the following events: (1) translocation of genomic DNA causes fusion of the human PTPRZ1 gene and the human MET gene so as to produce fused genomic DNA; (2) the fused genomic DNA is transcribed to obtain fused hnRNA; (3) the fused hnRNA is subjected to splicing to remove the introns and obtain mature fused mRNA; and (4) the mature fused mRNA is subjected to artificial reverse transcription to obtain the artificial synthetic cDNA. For example, as shown in FIG. 1, the human PTPRZ1 gene and the human MET gene are located on human chromosome 7. The translocation of genomic DNA causes the genomic DNA from exon 1 to exon 8 of the human PTPRZ1 gene to fuse with the genomic DNA from exon 2 to the end of the human MET gene so as to produce fused genomic DNA. The fused hnRNA is transcribed and then subjected to splicing to remove the introns and obtain mature fused mRNA; and the mature fused mRNA is subjected to artificial reverse transcription to obtain the artificial synthetic cDNA, which in the direction from 5' to 3' is formed of a first nucleic acid fragment connected to a second nucleic acid fragment, wherein the first nucleic acid fragment is as shown in SEQ ID NO: 10, and the second nucleic acid fragment is as shown in SEQ ID NO: 11 or 12.

The sequence of fused nucleic acid coding the above-mentioned fused protein can be obtained by decoding according to an amino acid codon comparison table. Due to the existence of degeneracy of codons, the sequences of a plurality of fused nucleic acids coding the fused protein with the same amino acid sequence can be different from each other.

The artificial synthetic cDNA in the direction from 5' to 3' is formed of a first nucleic acid fragment connected to a second nucleic acid fragment, wherein the first nucleic acid fragment is as shown in SEQ ID NO: 7, 8, 9 or 10, and the second nucleic acid fragment is as shown in SEQ ID NO: 11 or 12.

SEQ ID NO: 7 corresponds to a fragment of the translated region of the first exon of the human PTPRZ1 gene, coding the protein fragment as shown in SEQ ID NO: 1.

SEQ ID NO: 8 corresponds to the translated region of the sequence from the first exon to the second exon of the human PTPRZ1 gene, coding the protein fragment as shown in SEQ ID NO: 2.

SEQ ID NO: 9 corresponds to the translated region of the sequence from the first exon to the third exon of the human PTPRZ1 gene, coding the protein fragment as shown in SEQ ID NO: 3.

SEQ ID NO: 10 corresponds to the translated region of the sequence from the first exon to the eighth exon of the human PTPRZ1 gene, coding the protein fragment as shown in SEQ ID NO: 4.

The sequence of SEQ ID NO: 11 corresponds to the fragment starting from exon 2 of the homology isoform 1 of the human MET gene, coding the protein fragment as shown in SEQ ID NO: 5.

The sequence of SEQ ID NO: 12 corresponds to the fragment starting from exon 2 of the homology isoform 2 of the human MET gene, coding the protein fragment as shown in SEQ ID NO: 6.

In another aspect, the present invention further provides an artificial synthetic nucleic acid fragment, and the artificial synthetic nucleic acid fragment does not exist in the nature, wherein the sequence of the artificial synthetic nucleic acid fragment contains the sequence as shown in SEQ ID NO: 14, 15 or 16, and the artificial synthetic nucleic acid fragment is the fragment of the above-mentioned artificial synthetic cDNA.

The sequence of SEQ ID NO: 13 is the fragment of the fused nucleic acid formed of part of the 5'UTR, SEQ ID NO: 7 connected to a respective 5' part of SEQ ID NO: 11 or 12; and is obtained by performing PCR amplification with a first primer as shown in SEQ ID NO: 17 and a second primer as shown in SEQ ID NO: 18 by taking the cDNA as a template.

The sequence of SEQ ID NO: 14 is the fragment of the fused nucleic acid formed of part of the 5'UTR, SEQ ID NO: 8 connected to a respective 5' part of SEQ ID NO: 11 or 12; and is obtained by performing PCR amplification with the first primer as shown in SEQ ID NO: 17 and the second primer as shown in SEQ ID NO: 18 by taking the cDNA as the template.

The sequence of SEQ ID NO: 15 is the fragment of the fused nucleic acid formed of part of the 5'UTR, SEQ ID NO: 9 connected to a respective 5' part of SEQ ID NO: 11 or 12; and is obtained by performing PCR amplification with the first primer as shown in SEQ ID NO: 17 and the second primer as shown in SEQ ID NO: 18 by taking the cDNA as the template.

The sequence of SEQ ID NO: 16 is the fragment of the fused nucleic acid formed of part of the 5'UTR, of SEQ ID NO: 10 connected to a respective 5' part of SEQ ID NO: 11 or 12; and is obtained by performing PCR amplification with the first primer as shown in SEQ ID NO: 17 and the second primer as shown in SEQ ID NO: 18 by taking the cDNA as the template.

The sequence of the artificial synthetic nucleic acid fragment is the sequence as shown in SEQ ID NO: 14, 15 or 16.

In still another aspect, the present invention further provides a primer pair, wherein the primer pair contains a first primer as shown in SEQ ID NO: 17 and a second primer as shown in SEQ ID NO: 18, and 5' ends of the first primer and the second primer are chemically modified.

The present invention further provides a method for detecting secondary glioblastoma, the method comprising the following steps:

detecting a certain fused protein in a glioblastoma sample to be detected by using an artificially prepared antibody, wherein the fused protein in the direction from an N terminal to a C terminal is formed by connecting a first protein fragment and a second protein fragment, wherein the first protein fragment is as shown in SEQ ID NO: 1, 2, 3, or 4 and the second protein fragment is as shown in SEQ ID NO: 5 or 6; and indicating that the glioblastoma sample to be detected is the secondary glioblastoma if the fused protein is presented in the glioblastoma sample to be detected;

Additionally or alternatively, the method comprises the following steps:

detecting a certain fused nucleic acid in a glioblastoma sample to be detected by using a chemically modified nucleic acid probe and/or primers which are prepared artificially, wherein the fused nucleic acid is the nucleic acid coding the fused protein; and indicating that the glioblastoma sample to be detected is the secondary glioblastoma if the fused nucleic acid is presented in the glioblastoma sample to be detected.

The artificially prepared antibody can be a commercially available antibody and can also be the antibody prepared through a conventional monoclonal antibody and/or polyclonal antibody preparation technology. The chemical modification of the nucleic acid probe and/or the chemical modification in the primers can adopt various chemical modifications which are conventionally used in the probe and the primers, for example, the chemical modifications can comprise at least one of phosphorylation modification, biotin modification, digoxin modification, amino-modification and mercapto-modification.

According to the present invention, the average median survival time in the cases with the secondary glioblastoma, in which the fused protein of the invention appeared, was shorter than the average median survival time in the reported cases with the secondary glioblastoma, indicating that in the secondary glioblastoma, the cases in which the fused protein of the invention appeared had poorer prognosis. The fused protein provided by the present invention can also be used as a molecular marker for judging the prognosis of the secondary glioblastoma.

The present invention will be described below in detail through the Examples.

Preparation Example 1

In this preparation example, secondary glioblastoma samples and primary glioblastoma samples were obtained, and RNA and cDNA of the samples were further obtained.

TABLE 1

| No. of case | Gender | Age | Type of disease |
|---|---|---|---|
| 1 | M | 44 | pGBM |
| 2 | F | 59 | pGBM |
| 3 | F | 56 | pGBM |
| 4 | F | 48 | pGBM |
| 5 | M | 64 | pGBM |
| 6 | M | 66 | pGBM |
| 7 | M | 59 | pGBM |
| 8 | F | 62 | pGBM |
| 9 | M | 42 | pGBM |
| 10 | M | 81 | pGBM |
| 11 | M | 60 | pGBM |
| 12 | M | 29 | sGBM |
| 13 | M | 26 | pGBM |
| 14 | M | 47 | pGBM |
| 15 | M | 42 | pGBM |
| 16 | F | 43 | pGBM |
| 17 | F | 40 | sGBM |
| 18 | M | 27 | sGBM |
| 19 | M | 42 | pGBM |
| 20 | F | 37 | sGBM |
| 21 | M | 45 | sGBM |
| 22 | M | 54 | sGBM |
| 23 | F | 47 | sGBM |
| 24 | M | 33 | pGBM |
| 25 | M | 63 | pGBM |
| 26 | M | 34 | pGBM |
| 27 | M | 18 | sGBM |
| 28 | M | 33 | sGBM |
| 29 | M | 30 | pGBM |
| 30 | M | 49 | pGBM |
| 31 | M | 43 | pGBM |
| 32 | F | 28 | pGBM |

TABLE 1-continued

| No. of case | Gender | Age | Type of disease |
|---|---|---|---|
| 33 | M | 42 | sGBM |
| 34 | F | 62 | pGBM |
| 35 | M | 48 | pGBM |
| 36 | F | 51 | sGBM |
| 37 | F | 40 | pGBM |
| 38 | F | 24 | pGBM |
| 39 | F | 49 | sGBM |
| 40 | M | 51 | sGBM |
| 41 | F | 55 | pGBM |
| 42 | M | 38 | sGBM |
| 43 | M | 54 | pGBM |
| 44 | F | 60 | pGBM |
| 45 | F | 37 | pGBM |
| 46 | F | 59 | pGBM |
| 47 | M | 54 | pGBM |
| 48 | M | 52 | pGBM |
| 49 | M | 46 | pGBM |
| 50 | M | 56 | pGBM |
| 51 | M | 60 | pGBM |
| 52 | F | 63 | pGBM |
| 53 | M | 44 | pGBM |
| 54 | F | 25 | pGBM |
| 55 | M | 42 | pGBM |
| 56 | M | 51 | pGBM |
| 57 | M | 45 | pGBM |
| 58 | F | 50 | sGBM |
| 59 | M | 61 | pGBM |
| 60 | M | 43 | pGBM |
| 61 | F | 54 | pGBM |
| 62 | M | 39 | pGBM |
| 63 | M | 57 | pGBM |
| 64 | F | 64 | pGBM |
| 65 | F | 55 | pGBM |
| 66 | F | 52 | pGBM |
| 67 | M | 57 | pGBM |
| 68 | F | 60 | pGBM |
| 69 | M | 42 | pGBM |
| 70 | M | 46 | sGBM |
| 71 | M | 55 | pGBM |
| 72 | M | 44 | pGBM |
| 73 | M | 57 | pGBM |
| 74 | M | 45 | sGBM |
| 75 | M | 55 | pGBM |
| 76 | M | 40 | pGBM |
| 77 | F | 30 | sGBM |
| 78 | M | 25 | sGBM |
| 79 | M | 51 | sGBM |

By using the operation which is in line with the standard of Medical Ethics Committee, 59 cases of primary glioblastoma samples and 20 cases of secondary glioblastoma samples were collected. For each patient from whom the sample was collected, the consents of the patient and a therapist thereof were obtained, and written proofing materials were also possessed. The diagnosis, the identification, and the differentiation of the primary glioblastoma from the secondary glioblastoma were performed according to a histological method in the literature (Louis D N, et al, 2007. The 2007 WHO classification of tumors of the central nervous system. Acta Neuropathol 114 (2): 97-109). The information of the gender, the age, and the type of the disease of each pathological sample is as shown in Table 1, wherein pGBM represents the primary glioblastoma and sGBM represents the secondary glioblastoma.

A DNA extraction kit (purchased from Qiagen) was used to extract total RNA in the primary glioblastoma samples and the secondary glioblastoma samples according to an operation instruction. By detecting the total RNA by an integrity analyzer, it was confirmed that the RNA integrity number (RIN) was greater than 7.0. A reverse transcription kit (purchased from Invitrogen) was used for synthesizing double-stranded cDNA by using the total RNA as the template according to the operation instruction.

Example 1

In this example, RNA sequencing was performed on 59 cases of the primary glioblastoma samples and 20 cases of the secondary glioblastoma samples collected in the preparation example 1.

An RNA library construction kit (purchased from Illumina) was used for constructing an RNA library for the RNA of each sample, and then a sequencing platform (Illumina HiSeq 2000) was used for performing RNA sequencing on each RNA library. The sequences obtained by sequencing were aligned with a reference RNA sequence database (Hg19 Refseq, GRCh37), and the RNA of a fused gene was sought by referring to a method in the literature (McPherson A, et al. 2011. deFuse: an algorithm for gene fused discovery in tumor RNA-Seq data. PLoS Comput Biol 7(5): e1001138).

The results indicate that in the samples as shown in Table 1, the RNA of the fused gene of the present invention is present in a plurality of secondary glioblastoma (sGBM) samples, but the RNA of the fused gene of the present invention is not present in the primary glioblastoma (pGBM) samples. The specific appearance situations are as shown in Table 2.

TABLE 2

| | Fused gene | | Fused protein | | No. of cases with appearance | |
|---|---|---|---|---|---|---|
| | | | First | Second | Primary | Secondary |
| No. | First nucleic acid fragment | Second nucleic acid fragment | protein fragment | protein fragment | glioblastoma (pGBM) | glioblastoma (sGBM) |
| 1 | SEQ ID NO: 7 | SEQ ID NO: 11 | SEQ ID NO: 1 | SEQ ID NO: 5 | 0 | 2 |
| 2 | SEQ ID NO: 8 | SEQ ID NO: 11 | SEQ ID NO: 2 | SEQ ID NO: 5 | 0 | 1 |
| 3 | SEQ ID NO: 9 | SEQ ID NO: 11 | SEQ ID NO: 3 | SEQ ID NO: 5 | 0 | 4 |
| 4 | SEQ ID NO: 10 | SEQ ID NO: 11 | SEQ ID NO: 4 | SEQ ID NO: 5 | 0 | 2 |
| 5 | SEQ ID NO: 7 | SEQ ID NO: 12 | SEQ ID NO: 1 | SEQ ID NO: 6 | 0 | 5 |
| 6 | SEQ ID NO: 8 | SEQ ID NO: 12 | SEQ ID NO: 2 | SEQ ID NO: 6 | 0 | 3 |
| 7 | SEQ ID NO: 9 | SEQ ID NO: 12 | SEQ ID NO: 3 | SEQ ID NO: 6 | 0 | 1 |
| 8 | SEQ ID NO: 10 | SEQ ID NO: 12 | SEQ ID NO: 4 | SEQ ID NO: 6 | 0 | 2 |
| | | | | Total | 0 | 20 |

It could be seen from the data in Table 2 that the fused protein described in the present invention specifically appeared in the secondary glioblastoma rather than the primary glioblastoma, so that the fused protein could be used for distinguishing the secondary glioblastoma from the primary glioblastoma. FIG. 1 illustrates the formation process of the fused gene of the present invention as an example, namely, it shows a structural schematic diagram formed by connecting a PTPRZ1 protein fragment and an MET protein fragment.

In addition, according to the calculation, the average median survival time in the cases with the secondary glioblastoma, in which the fused protein of the present invention appeared was 127 days, which was shorter than the average median survival time (248 days) in the reported cases with the secondary glioblastoma, indicating that in the secondary glioblastoma, the cases in which the fused protein of the present invention appeared had poorer prognosis.

Example 2

In this example, PCR verification of the fused protein was performed on the RNA obtained from the 59 cases of the primary glioblastoma samples and the 20 cases of the secondary glioblastoma samples collected in the preparation example 1.

Primers used for PCR verification comprises a first primer as shown in SEQ ID NO: 17 and a second primer as shown in SEQ ID NO: 18. The operation of the PCR was performed according to the synthetic primers and an instruction of a PCR kit. The presence of an amplification band in each PCR product was displayed by agarose gel nucleic acid electrophoresis, and each presented amplification band was recovered by using a DNA gel recovery kit (QIAquick PCR purification kit, purchased from Qiagen), then cloned to a T vector (pGEM-T easy vector, purchased from Promega) and then sequenced by using a DNA sequencer (ABI Prism 3730×1 DNA Sequencer, purchased from Applied Biosystems). The results are as shown in Table 3.

cally, the secondary glioblastoma and the primary glioblastoma can be distinguished by using the PCR method.

In addition, according to the calculation, the average median survival time in the cases with the secondary glioblastoma, in which the fused protein of the invention was presented was 127 days, which was shorter than the average median survival time (248 days) in the reported cases with the secondary glioblastoma, indicating that in the secondary glioblastoma, the cases in which the fused protein of the present invention was presented had poorer prognosis.

In addition, for those samples having cDNA in which the products as shown in SEQ ID: NO: 13-16 have been amplified, the genomic DNA were used as templates to conduct PCR amplifications, by using the first primer as shown in SEQ ID NO: 17 and the second primer as shown in SEQ ID NO: 18, and it was found that in the amplification products of genomic DNA, the product as shown in SEQ ID NO: 13 was present, but the products as shown in SEQ ID NO: 14-16 were not present. The possible reason was that in the genomic DNA of the samples in which the fused gene was present, the nucleic acid fragment as shown in SEQ ID NO: 13 was present between a site as shown in SEQ ID NO: 17 and the site as shown in SEQ ID NO: 18 in the genomic DNA, while the nucleic acid fragments as shown in SEQ ID NO: 14-16 were not present between those sites.

Example 3

In this example, immuno-hybridization verification of the fused protein was performed on the total protein samples of the 59 cases of the primary glioblastoma samples and the 20 cases of the secondary glioblastoma samples collected in the preparation example 1.

An antibody used for immuno-hybridization verification was an anti-human MET protein antibody (the antibody was derived from a rabbit and purchased from Abcam, and the product number was ab51067). The size of the non-fused

TABLE 3

|     | Fused gene | | Fused protein | | Sequence of | No. of cases | |
|     | --- | --- | --- | --- | --- | --- | --- |
| No. | First nucleic acid fragment | Second nucleic acid fragment | First protein fragment | Second protein fragment | amplification product | Primary glioblastoma (pGBM) | Secondary glioblastoma (sGBM) |
| 1 | SEQ ID NO: 7  | SEQ ID NO: 11 | SEQ ID NO: 1 | SEQ ID NO: 5 | SEQ ID NO: 13 | 0 | 2 |
| 2 | SEQ ID NO: 8  | SEQ ID NO: 11 | SEQ ID NO: 2 | SEQ ID NO: 5 | SEQ ID NO: 14 | 0 | 1 |
| 3 | SEQ ID NO: 9  | SEQ ID NO: 11 | SEQ ID NO: 3 | SEQ ID NO: 5 | SEQ ID NO: 15 | 0 | 4 |
| 4 | SEQ ID NO: 10 | SEQ ID NO: 11 | SEQ ID NO: 4 | SEQ ID NO: 5 | SEQ ID NO: 16 | 0 | 2 |
| 5 | SEQ ID NO: 7  | SEQ ID NO: 12 | SEQ ID NO: 1 | SEQ ID NO: 6 | SEQ ID NO: 13 | 0 | 5 |
| 6 | SEQ ID NO: 8  | SEQ ID NO: 12 | SEQ ID NO: 2 | SEQ ID NO: 6 | SEQ ID NO: 14 | 0 | 3 |
| 7 | SEQ ID NO: 9  | SEQ ID NO: 12 | SEQ ID NO: 3 | SEQ ID NO: 6 | SEQ ID NO: 15 | 0 | 1 |
| 8 | SEQ ID NO: 10 | SEQ ID NO: 12 | SEQ ID NO: 4 | SEQ ID NO: 6 | SEQ ID NO: 16 | 0 | 2 |
|     | Total | | | | | 0 | 20 |

It can be seen from the data in Table 3 that the fragment of the fused gene described in the present invention is specifically presented in the secondary glioblastoma rather than the primary glioblastoma, so that the fragment of the fused gene can be used for distinguishing the secondary glioblastoma from the primary glioblastoma; and specifihuman MET protein was 145 kDa, while the molecular weight of the fused protein was increased. The operation of immuno-hybridization was performed by referring to the instruction of the antibody and the instruction of an immuno-hybridization kit. The presence and the positions of immuno-hybridization bands are as shown in Table 4.

TABLE 4

| No. | Fused gene | | Fused protein | | Size of fused hybridization band (kDa) | Cases in which fused hybridization band presents | |
|---|---|---|---|---|---|---|---|
| | | | | | | Primary glioblastoma (pGBM) | Secondary glioblastoma (sGBM) |
| | First nucleic acid fragment | Second nucleic acid fragment | First protein fragment | Second protein fragment | | | |
| 1 | SEQ ID NO: 7  | SEQ ID NO: 11 | SEQ ID NO: 13 | SEQ ID NO: 5 | 158 | 0 | 2 |
| 2 | SEQ ID NO: 8  | SEQ ID NO: 11 | SEQ ID NO: 14 | SEQ ID NO: 5 | 160 | 0 | 1 |
| 3 | SEQ ID NO: 9  | SEQ ID NO: 11 | SEQ ID NO: 15 | SEQ ID NO: 5 | 167 | 0 | 4 |
| 4 | SEQ ID NO: 10 | SEQ ID NO: 11 | SEQ ID NO: 16 | SEQ ID NO: 5 | 191 | 0 | 2 |
| 5 | SEQ ID NO: 7  | SEQ ID NO: 12 | SEQ ID NO: 13 | SEQ ID NO: 6 | 159 | 0 | 5 |
| 6 | SEQ ID NO: 8  | SEQ ID NO: 12 | SEQ ID NO: 14 | SEQ ID NO: 6 | 161 | 0 | 3 |
| 7 | SEQ ID NO: 9  | SEQ ID NO: 12 | SEQ ID NO: 15 | SEQ ID NO: 6 | 168 | 0 | 1 |
| 8 | SEQ ID NO: 10 | SEQ ID NO: 12 | SEQ ID NO: 16 | SEQ ID NO: 6 | 192 | 0 | 2 |
| | | | Total | | | 0 | 20 |

It can be seen from the data in Table 4 that the protein expression product of the fused gene described in the present invention is specifically present in the secondary glioblastoma rather than in the primary glioblastoma, so that the protein expression product of the fused gene can be used for distinguishing the secondary glioblastoma from the primary glioblastoma; and specifically, the secondary glioblastoma and the primary glioblastoma can be distinguished by using the immuno-hybridization method.

In addition, according to the calculation, the average median survival time in the cases with the secondary glioblastoma, in which the fused protein of the present invention appeared was 127 days, which was shorter than the average median survival time (248 days) in the reported cases with the secondary glioblastoma, indicating that in the secondary glioblastoma, the cases in which the fused protein of the invention was presented had poorer prognosis.

Comparative Example 1

According to a method in the literature (Yan H, et al. 2009. IDH1 and IDH2 mutations in gliomas. N Engl J Med 360(8): 765-773), presence of the mutation of isocitrate dehydrogenase (IDH) was tested in the 20 cases of secondary glioblastoma (sGBM) in the preparation example 1, and it was found from the results that the mutation of IDH only occurred in 12 cases. Thus, the distinguishing of the secondary glioblastoma from the primary glioblastoma by means of the mutation of IDH had relatively low accuracy.

The preferred embodiments of the present invention are described in detail in conjunction with the accompanying drawing. However, the present invention is not limited to the specific details in the embodiments, and in the scope of technical concept, the technical scheme of the present invention can be subjected to a variety of simple modifications, and these simple modifications still belong to the scope of protection of the present invention.

In addition, it needs to be noted that the various specific technical features described in the above embodiments can be combined in any suitable way under the situation that no contradictions exist. In order to avoid the unnecessary repetition, the various possible combination ways will not be described any more herein.

In addition, the various different embodiments of the present invention can also be combined arbitrarily, and the combinations should also be considered as the contents disclosed in the invention as long as the combinations do not depart from the idea of the present invention.

The invention claimed is:

1. A method for detecting secondary glioblastoma, the method comprising the following steps:
   detecting a certain fused nucleic acid in a glioblastoma sample by using a nucleic acid probe and/or primers with chemical modifications,
   wherein the chemical modifications comprise at least one of phosphorylation modification, biotin modification, digoxin modification, amino-modification and mercapto-modification,
   wherein the nucleic acid probe and/or primers comprise at least one of a primer having a sequence of SEQ ID NO: 17 and a primer having a sequence of SEQ ID NO: 18;
   wherein said fused nucleic acid is a nucleic acid encoding a fused protein, and
   wherein in a direction from an N terminal to a C terminal, said fused protein is formed of a first protein fragment connected to a second protein fragment, wherein said first protein fragment is as shown in SEQ ID NO: 1, 2, 3, or 4 and said second protein fragment is as shown in SEQ ID NO: 5 or 6; and
   indicating that said glioblastoma sample is a secondary glioblastoma if the fused nucleic acid is detected in the glioblastoma sample.

* * * * *